United States Patent

Mahoney et al.

[11] Patent Number: 5,820,874
[45] Date of Patent: Oct. 13, 1998

[54] ALGINATE FIBRES, METHOD OF PREPARATION AND USE

[75] Inventors: Peter M. J. Mahoney, Powys; Anne Elizabeth Howells, West Glamorgan, both of Great Britain

[73] Assignee: Bristol-Myers Squibb Company, New York, N.Y.

[21] Appl. No.: 765,908

[22] PCT Filed: Jul. 14, 1995

[86] PCT No.: PCT/EP95/02771

§ 371 Date: May 30, 1997

§ 102(e) Date: May 30, 1997

[87] PCT Pub. No.: WO96/02283

PCT Pub. Date: Feb. 1, 1996

[30] Foreign Application Priority Data

Jul. 15, 1994 [GB] United Kingdom ............... 9414303

[51] Int. Cl.[6] .................... A61F 13/00; A61K 9/70
[52] U.S. Cl. .................... 424/443; 424/444; 424/484; 424/488; 424/DIG. 13
[58] Field of Search .................... 424/443, 444, 424/484, 488, DIG. 13

[56] References Cited

U.S. PATENT DOCUMENTS

| 4,948,575 | 8/1990 | Cloe et al. | 424/44 |
| 5,238,685 | 8/1993 | Wren | 424/445 |
| 5,256,477 | 10/1993 | Mahoney | 428/283 |
| 5,482,932 | 1/1996 | Thompson | 514/54 |
| 5,523,093 | 6/1996 | Della Valle et al. | 424/444 |
| 5,540,922 | 7/1996 | Fabo | 424/402 |
| 5,618,561 | 4/1997 | Della Valle et al. | 424/488 |

Primary Examiner—Thurman K. Page
Assistant Examiner—Kathryne E. Shelborne
Attorney, Agent, or Firm—John M. Kilcoyne; Theodore R. Furman, Jr.

[57] ABSTRACT

The present invention is concerned with alginate fibres, and in particular the use thereof as a wound dressing and a method of preparing the same. There is provided alginate fibres for use in the absorption of at least 10% by weight based on the weight of the alginate fibres of proteinaceous material from a wound environment into the structure of the fibres.

21 Claims, 5 Drawing Sheets

Fig. 2 TGA

ALGINATE FIBRES, METHOD OF PREPARATION AND USE

This application is a 35 USC 371 of PCT/EP95/2771 filed Jul. 24, 1995.

The present invention is concerned with alginate fibres, and in particular the use thereof as a wound dressing and a method of preparing the same.

Alginate fibres have been known for some time as being useful in the preparation of alginate fabric wound dressings. A number of methods for producing conventional alginate fibres are described in the art. The extrusion of alginate solutions into an aqueous solution containing calcium ions to form calcium alginate filaments is known, for example, from British Patent Specifications Nos. 567641, 568177, 571657 and 624987. The replacement of a proportion of the calcium ions in calcium alginate by sodium ions to produce a more soluble fibre is known from British Patent Specification No. 653341.

Wound dressings including alginate fibres are known to be useful in the treatment of heavily exuding wounds. For example EP 0476756 describes a fabric of alginate fibres suitable for use in the treatment of heavily exuding wounds, the fabric having an absorbency of greater than 25.0 grams of deionised water per gram of fabric. Where a wound is heavily exuding, the use of a high absorbency wound dressing is advantageous in achieving efficient uptake of exudate, together with its associated toxins and other desirable matter, such as proteases and the like.

The presence of proteinaceous material, such as proteases and the like, in a wound environment can be detrimental to the recovery process of the wound. For example, growth factors may be degraded by proteases which could impede the general recovery of the wound. It has therefore been common practice to remove slough, which contains the above described detrimental proteases, from a wound environment to enhance the recovery process. The recovery can be observed by the change of a yellow wound containing a large quantity of slough to a red or pink granulating wound.

Conventionally, proteases are often removed from a wound environment by employing commercially available DEXRANOMER beads or paste which are subsequently removed by irrigation. Removal of the above products can be somewhat traumatic and this problem can be alleviated by the use of a fibrous product, such as alginate wound dressings. However, known alginate dressings take up proteases into the interstitial spaces between the fibres of the fabric and this limits the amount of protease uptake which can be achieved. For example, an alginate wound dressing such as that available under the trade mark KALTOSTAT has been found to have a protease uptake of the order of 4% by weight of the dressing, which can result in the undesirable retention of proteases in the wound environment.

It is therefore desirable to provide a wound dressing, capable of exhibiting improved absorptive properties with respect to proteases present in a wound environment. Alginate fibres have now been discovered suitable for use in the treatment of wounds which alleviate the above problems.

According to the present invention there is provided alginate fibres for use in the absorption of proteinaceous material from a wound environment into the structure of the fibres.

Absorption into the structure of the fibres as referred to above denotes uptake into the fibres themselves as opposed to solely the interstitial spaces therebetween. The ability of alginate fibres to take up proteinaceous material into the structure of the fibre results in considerably improved absorptive properties. The improved absorptive properties resulting from the uptake of proteinaceous material into the structure of the fibres, as opposed to the intersititial spaces between the fibres in an alginate fabric can be seen with reference to the accompanying examples. More specifically, conventional alginate such as that available under the trade mark KALTOSTAT has a protease uptake as described above of the order of 4% by weight, based on the weight of the alginate, whereas alginate fibres capable of absorbing proteases into the structure of the fibres can have a protease uptake as high as 50 to 60% by weight, based on the weight of the alginate.

Advantageously, the proteinaceous material absorbed into the structure of the fibres comprises proteases. As hereinbefore described, it is desirable to remove proteases from a wound environment in order to enhance recovery of a wound. Recovery of a wound can be further enhanced by the present invention by the uptake, into the structure of the alginate fibres, of other components present in the wound environment. This can often result in the viscocity of a thick wound exudate being reduced due to the uptake of compounds therefrom. In particular, haemoglobin can be absorbed into the structure of the fibres, resulting in a thinner exudate and an accompanying change in colour thereof from a red or pink exudate to a clear exudate. Skilled addressees will appreciate that the above change in the exudate will aid recovery of the wound.

Accordingly there is further provided by the present invention alginate fibres for use in the absorption of proteases from a wound environment into the structure of the fibres.

Suitably at least 10% by weight, based on the weight of the alginate fibres, of proteinaceous material, preferably proteases, are absorbed into the structure of the alginate fibres employed according to the present invention. More preferably at least 30%, and in particular 50 to 60% by weight, based on the weight of the alginate fibres, of proteinaceous material, preferably proteases, are absorbed.

There is further provided by the present invention alginate fibres for use in absorbing at least 10% by weight, based on the weight of the fibres, of proteases from a wound environment into the structure of the alginate fibres.

Use of alginate fibres substantially as hereinbefore described according to the present invention suitably involves debriding of a wound. The term "debriding" as used herein describes general removal from a wound of undesirable material such as proteases, and includes within its scope both desloughing and the removal of a hard eschar from a wound site.

In a first embodiment of the present invention use of alginate fibres in the absorption, into the structure of the fibres, of proteinaceous materials from a wound environment, involves use of the fibres in desloughing the wound environment whereby proteases are absorbed into the structure of the alginate fibres. This desloughing is accompanied by an observable change of the wound environment from a yellow sloughy wound to a red granulating wound. In desloughing of the wound environment, the alginate fibres may be applied to the wound in a wetted or dry state, although it is preferred that the fibres are applied in a wetted state.

In a second embodiment of the present invention wherein the fibres are employed in the removal of a hard eschar from a wound environment, the alginate fibres are employed in a wetted state so as to solubilise the eschar and allow protease uptake from the solubilised eschar and surrounding environment.

There is further provided by the present invention a method of treating a wound, which method comprises applying alginate fibres to the wound so as to effect uptake of proteinaceous material from the wound into the structure of the alginate fibres.

As hereinafter described advantageously the proteinaceous material comprises proteases, and there is further provided by the present invention a method of treating a wound, which method comprises applying alginate fibres to the wound so as to effect uptake of proteases from the wound into the structure of the fibre.

Aptly a method according to the present invention involves the uptake of at least 10% by weight, based on the weight of the alginate fibres, of proteinaceous material, preferably proteases, into the structure of the fibres. More preferably at least 30%, and in particular 50 to 60% by weight, based on the weight of the alginate fibres, of proteinaceous material, preferably proteases, are absorbed into the structure of the fibres by a method according to the present invention.

According to the first embodiment of the present invention there is provided a method of treating a wound, whereby the alginate fibres are applied to a wound environment so as to effect uptake of slough into the structure of the fibres. Normally and preferentially associated proteases are taken up. A method according to the first embodiment of the present invention may involve applying the alginate fibres to a wound in a wetted or dry state, preferably in a wetted state. Accordingly, the method typically comprises applying the wetted fibres to the wound, and in some circumstances wetting the fibres prior to application.

The alginate fibres when employed in desloughing a wound according to the present invention may be wetted either with pure water or preferably with saline solution. The high water retention capability of the fibres will ensure that an appreciable supply of water is available from the wetted fibres, to the wound environment. A further advantage of the fibres is that they do not drip when applied to a curved surface such as an area of the human body, in contrast to conventional dressings such as surgical gauze and cotton wool which have a propensity to allow water to "run off".

The fibres may suitably be supplied in a pre-wetted state, or alternatively may be supplied in the dry state with instructions for wetting before application to a wound environment. If supplied in a pre-wetted state, the fibres will advantageously incorporate conventional preservatives, for example Metasol D3T (Merck), Parasept (methyl paraben) (Kaloma Chemical) or Bromopol (2-bromo-2-nitro-1,3-propanediol) (Boots Ltd.), in order to prevent or retard the biological degradation of the fibre constituents.

According to the second embodiment of the present invention there is provided a method of treating a wound, whereby the method comprises applying alginate fibres in a wetted state to a wound environment having a hard eschar thereon, thereby solubilising the eschar, and absorbing at least part of the solubilised eschar into the structure of the fibres. Normally and preferentially associated proteases are absorbed.

Wetting of the fibres for use according to the second embodiment of the present invention is achieved as described above with reference to the first embodiment of the present invention, whereby the fibres may be wetted with pure water or preferably with saline solution and may be supplied in a pre-wetted state or alternatively may be supplied in the dry state with instructions for wetting before application.

Suitably a method according to the present invention involves applying alginate fibres to a wound environment for a period selected from one to sixteen days, depending on the acuteness of the wound and the recovery observed. In the case of a rapidly healing, relatively non-acute wound the method involves applying the fibres to a wound environment for one to two days. Alternatively, in the case of an acute wound, such as a heavily exuding ulcer or burn, the method according to the present invention comprises applying the alginate fibres to the wound environment for up to sixteen days.

Aptly a method according to the present invention involves removal of the fibres the wound environment undergoing treatment on a once or twice daily basis. Aptly removal of the fibres involves irrigation with pure water or saline solution and may further comprise excision of the slough or eschar, by for example removal of the top layer of the slough or eschar.

Accordingly there is provided by the present invention a wound dressing comprising alginate fibres for use in the absorption of proteinaceous material, especially proteases, from a wound environment into the structure of the fibres.

A method according to the present invention typically comprises applying alginate fibres in the form of a wound dressing to a wound environment in a manner substantially as hereinbefore described.

Alginate fibres suitable for use in absorbing proteinaceous material into the structure of the fibres may be characterised by reference to their unique thermal properties. More specifically, the fibres can be characterised in that a plot of the first order derivative of percentage weight loss of the fibre with temperature against temperature has two maxima in the range of 100° to 400° C.

In general, the two maxima in the plot of the first order derivative of percentage weight loss with temperature against temperature for a fibre as described above will fall within the range 200° to 300° C., preferably 220° to 290° C.

Thermogravimetric analysis was performed using a 2950TGA manufactured by TA Instruments, Delaware, U.S.A. Differential scanning calorimetry (DSC) was performed using a DSC7 manufactured by Perkin-Elmer.

Figure 1:
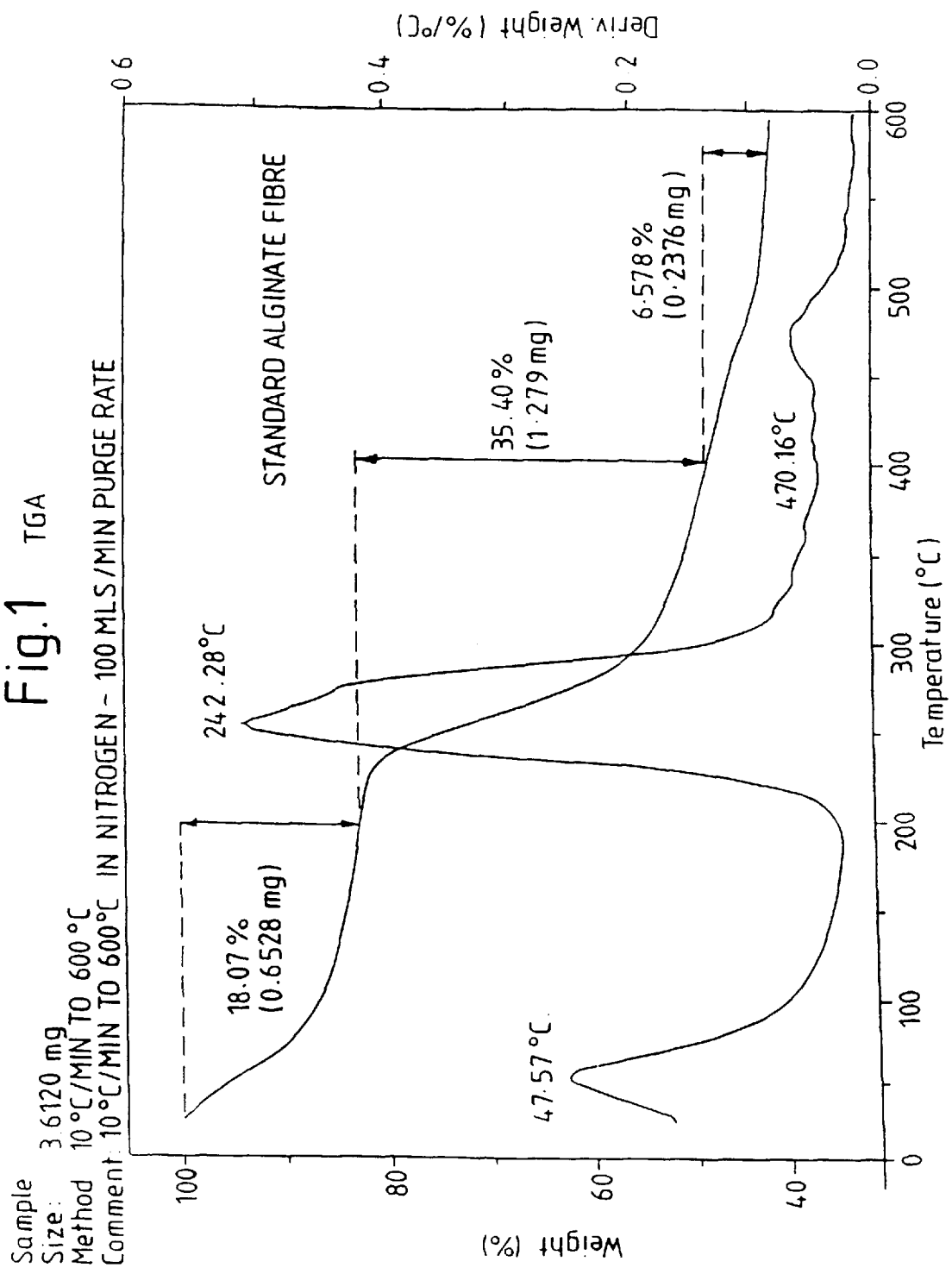
FIG. 1 shows the thermogravimetric analysis (TGA) of an 80:20 calcium:sodium alginate fibre prepared by conventional methods.
Figure 2:
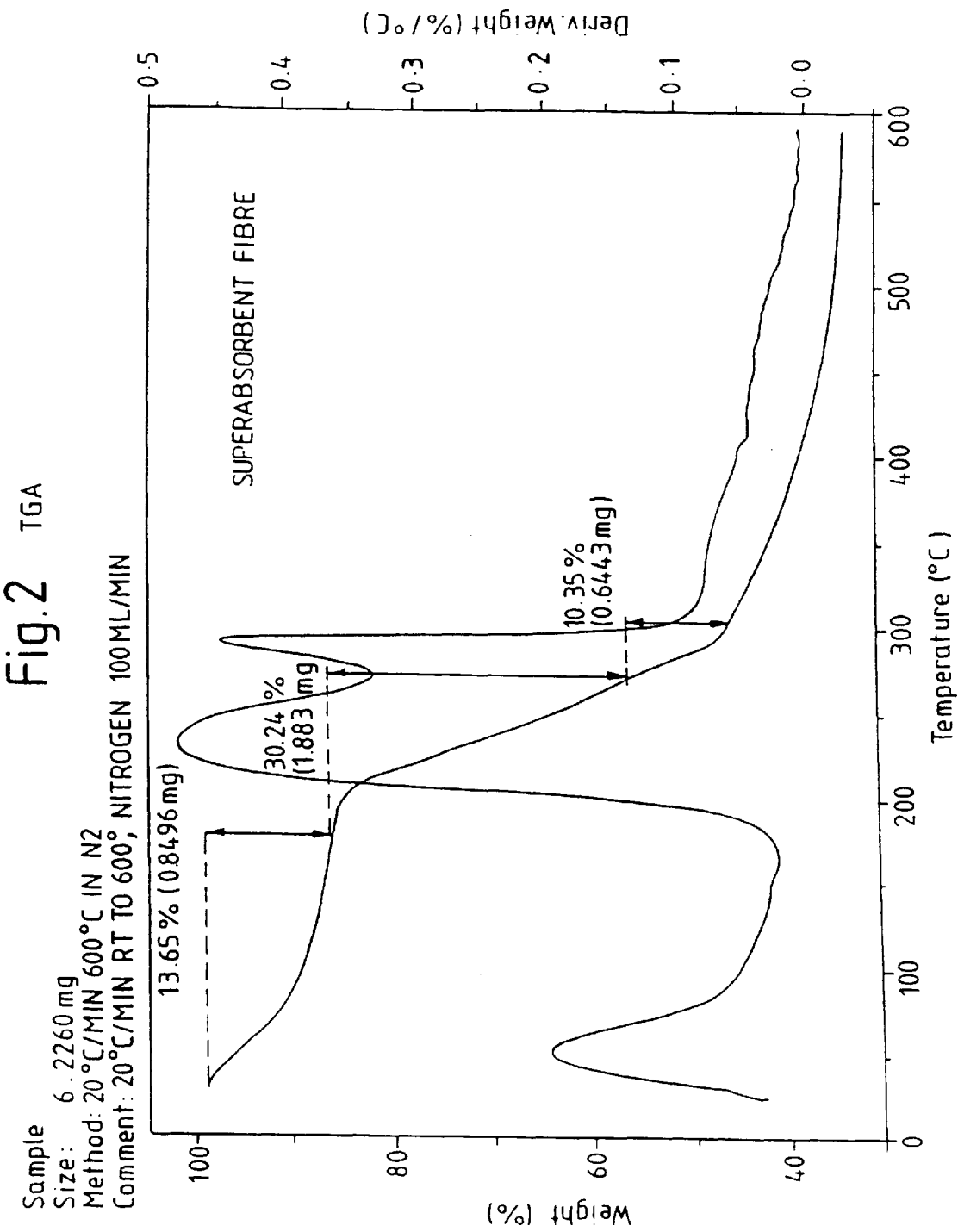
FIG. 2 shows the thermogravimetric analysis (TGA) of a fibre employed in the present invention, prepared from the same source material as the fibre of FIG. 1.

FIG. 1 shows the percentage weight loss of a conventional alginate fibre with increasing temperature, and the first order derivative of that function. The derivative shows a single maximum at approximately 240° C. In contrast, the first order derivative of percentage weight loss with temperature for a corresponding fibre employed according to the present invention, shown in FIG. 2, has two peaks, one at a lower temperature than the maximum observed for the conventional fibre (approximately 225° C.), and one at a higher temperature than the maximum observed for the conventional fibre (approximately 280° C.). This "splitting" of the derivative maximum for the conventional fibre of the same composition is characteristic of fibres employed according to the present invention.

Figure 3:
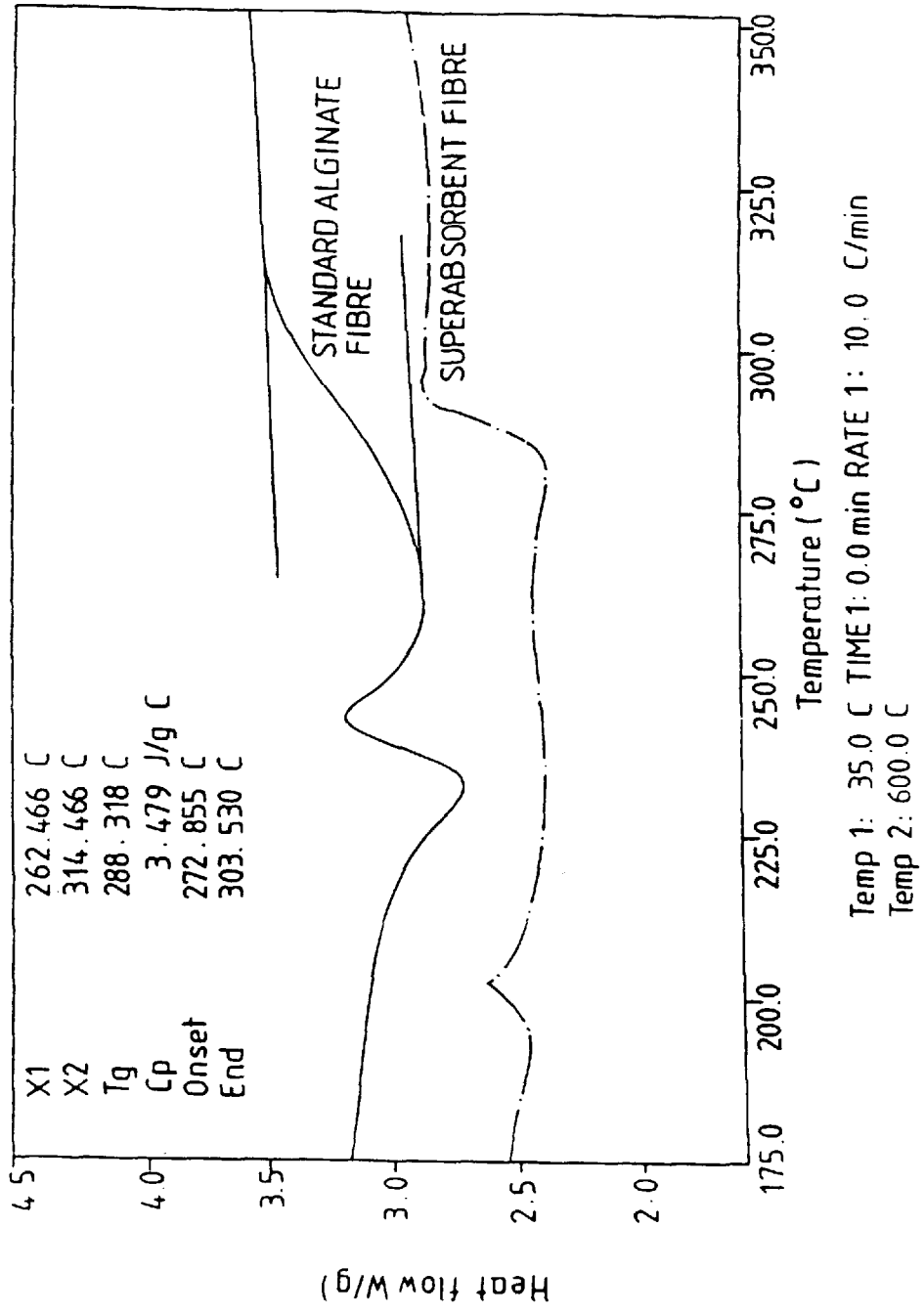
FIG. 3 shows the variation of heat flow with temperature for a conventional 80:20 calcium:sodium alginate fibre and a corresponding fibre employed in accordance with the present invention.
Figure 4:
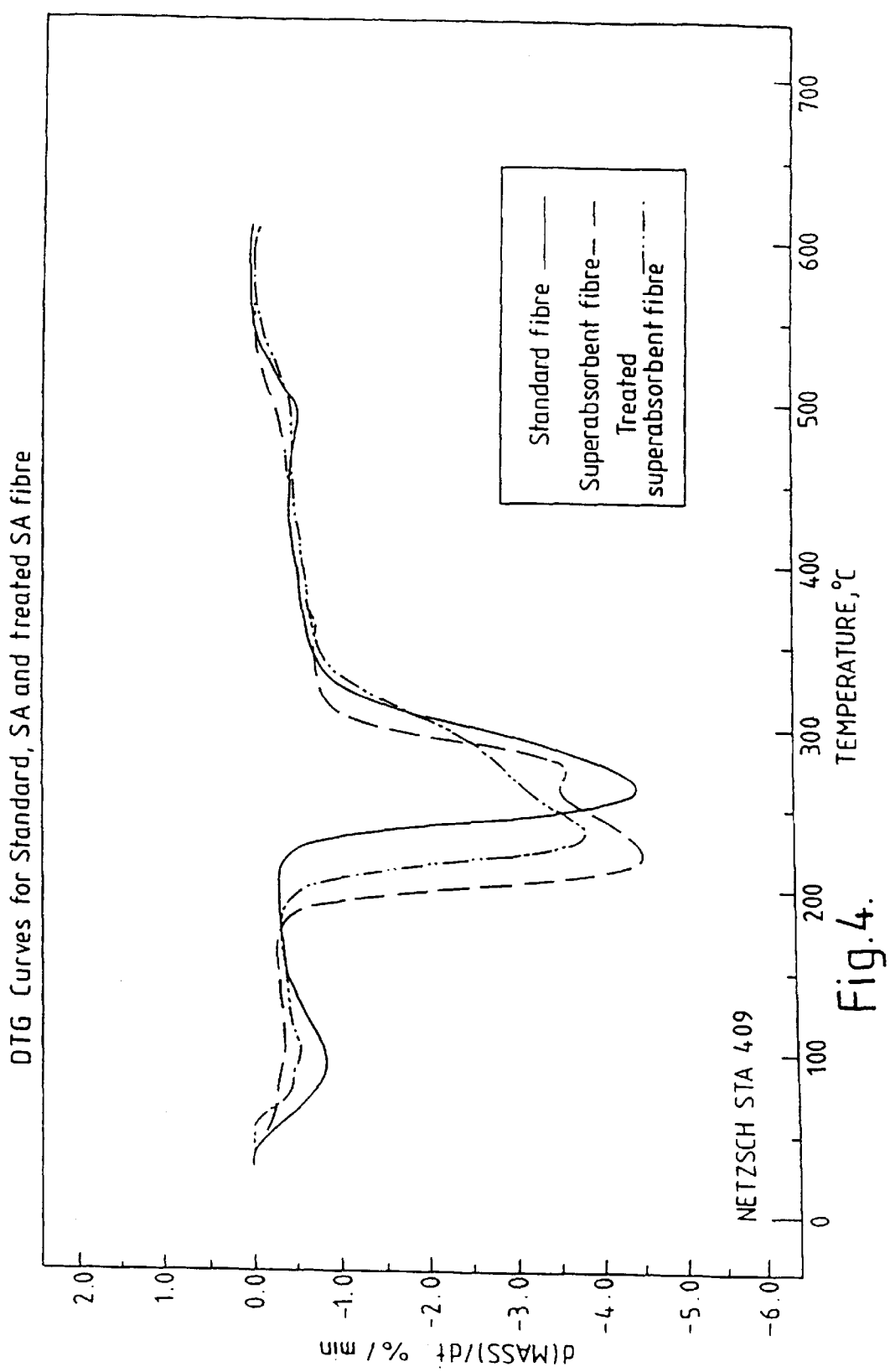
FIG. 4 shows the thermogravimetric analysis of a conventional fibre, a high absorbency fibre according to this invention and such a fibre treated with calcium ions.

FIG. 3 also shows differences in the thermal properties of a conventional alginate fibre and a fibre employed according to the present invention. Heat flow is effectively a measure of enthalpy associated with a transition, reaction or decomposition. The glass transition temperature (Tg) shown in FIG. 3 is the same for both fibres (288° C.). However, it can be seen that the transition for the conventional fibre is broad, occurring over some 50° C., whereas that for the fibre employed in accordance with the invention is sharp, taking place over less than 20° C.

In a further or alternative aspect, the present invention thus provides alginate fibre for use in the absorption of proteinaceous material from a wound environment into the structure of the fibre, characterised in that the glass transition temperature is less than 30° C., such as about 26° C.

Alginate fibres employed in fabrics according to the present invention can further be characterised in terms of their dielectric behaviour. For polymers the dielectric constant is dependent on the ease with which the polymer orientates itself in response to an applied field and this is a function of the structure of the polymer. The constant is most easily expressed in terms of the relationship between the in-phase and out-of-phase components of the dynamic field. This is conventionally expressed as Tanδ. Multiple peaks are normally recorded when measuring Tans due to a variety of relaxation phenomena. We have found that alginate fibres suitable for use in the fabrics of the present invention have Tanδ values in the range of less than 1 and up to 15 Hz. Conventional alginate fibres have Tanδ values of from 40 Hz to 7000 Hz.

Alginate fibres suitable for use according to the present invention can be prepared by the following steps:

(1) treating alginate fibres with a suitable acid so as to produce fibres comprising approximately 90–98%, such as 95%–98%, alginic acid fibres;

(2) treating the alginic acid fibres with a saturated aqueous solution of mono- or divalent cations;

(3) washing the fibres with water until imbibition of water by the fibres has effectively ceased;

(4) treating the fibres with a source of a cation capable of forming a water-soluble alginate salt.

The present invention also provides alginate fibres for use in the absorption of proteinaceous material from a wound environment into the structure of the fibres, characterised in that the fibres are prepared according to the above described process.

The fibres used as starting material in step 1 may be conventional salted alginate fibres (for example sodium, calcium, mixed sodium/calcium fibres produced in conventional manner, for example from 2–10% w/w solutions, for example 4 to 6% solution).

Most suitably the alginate fibres for use in step (1) are calcium alginate fibres. These fibres can be spun from a dope solution containing 2 to 10% by weight of sodium alginate, suitable 4 to 6% by weight of sodium alginate, employing techniques conventional in the art.

Suitable acids for use in step (1) include acids capable of protonating alginic acid and may include both organic and inorganic acids. Preferably, hydrochloric acid will be used. Preferably the resulting alginic acid fibres have at least 95% of the acid residues in the unsalted form.

Suitable mono- or divalent cations of use in step (2) include solutions of sodium, potassium and magnesium cations. Preferably a pharmaceutically acceptable monovalent cation is used, most preferably a sodium ion.

Step (3) is preferably effected by washing the fibres in a stream of deionised water. Desirably step (3) may be discontinued when swelling has ceased.

Cations capable of forming water-soluble alginate salts include, for example, sodium, potassium, lithium, ammonium and magnesium cations. Preferably the source of a cation capable of forming a water-soluble alginate salt used in step (4) is a source of sodium cations, more preferably sodium carbonate. Other carbonates may be used in like manner to produce the alternative salts.

Small quantities of other ions (for example zinc or silver) may be present in step (4) if desired but generally these may be included in the fibre after completion of step (4) if their presence is required.

A method of treating the product of the above process to include other ions is to treat the product with an aqueous solution of a source of the ions.

The fibres may be collected at the end of step (4) by filtration or other suitable method and may be dried, for example by treatment with acetone and then drying in air. It is one of the advantages of this invention that the highly absorbent fibres may be dried without losing their ability to be highly absorbent when rewetted.

The alginate may be obtained from any convenient source, for example *L. Hyperbola* or *Eclonia Maxima* of which *Eclonia Maxima* is preferred.

The fibres prepared according to the abovedescribed process may be dried using conventional methods, for example, using acetone or hot air drying.

Alginate fibres produced as above have considerably improved absorbency as compared to conventional alginate fibres.

Figure 5:
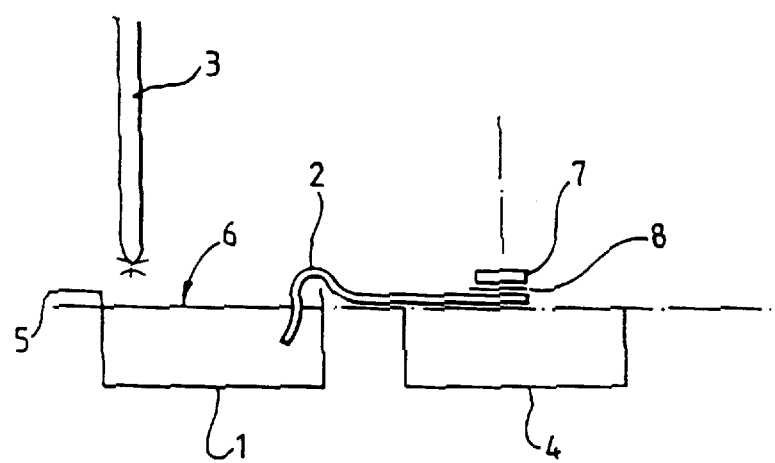
FIG. 5 shows apparatus suitable for determining absorbency.

Alginate fibres employed according to the present invention in the absorption of proteinaceous material present in a wound environment may be characterised in that the absorbency thereof is at least 40.0 grams of deionised water per gram of fibres as measured with reference to the test method depicted in FIG. 5 appended hereto.

The fibres have an absorbency of at least 40 times their own weight of deionised water and more aptly at least 60 times and most aptly at least 80 times their own weight of deionised water. Typically the fibres have an absorbency of much greater than this, for example 80 to 280 times their own weight, such as about 120 grams of deionised water per gram of fibre.

In a further aspect, the present invention provides an alginate fabric for use in the absorption of proteinaceous material present in a wound environment into the structure of the fibres, the fabric formed in whole or in part from the alginate fibres as hereinbefore described.

The solubility of the fibres may be modified by choosing the degree of neutralisation of the unsalted carbonyl groups by solubilizing ion. Thus for example, if a sheet of fibres (such as may be employed in a dressing) is required which is highly absorbent but which will remain intact as gelled fibres, the fibres are produced under conditions where a small proportion of residual carboxy groups is retained (for example by using insufficient $Na_2CO_3$ or the like to effect complete neutralisation). Alternatively, the material can be made fully soluble by replacing essentially all of the unsalted carboxy groups with a solubilizing ion such as sodium (for example by using at least a sufficient amount of $Na_2CO_3$ or the like to effect complete neutralisation).

Aptly the alginate fibres used according to the present invention comprise a mixed salt alginate which has first and second cations, the first cation being capable of forming an insoluble alginate salt and the second cation being capable of forming a soluble alginate salt. Suitably the first cation is calcium, although it will be appreciated that other cations such as zinc and the like could be employed. Typically the second cation comprises a solubilising cation such as sodium, potassium, lithium, ammonium, magnesium and the like, sodium being preferred.

Apt ratios of the first (insolubilising) to the second (solubilising) cations is in the range of 30:70% to 100:0% by weight. More suitably the ratio of insolubilising to solubilising cations is 70:30 to 100:0% by weight, and even more suitably 80:20 to 100:0% by weight.

A method of preparing fibres having a higher insolubilising ion content (such as calcium) than those prepared directly by the process as hereinbefore described which employs sufficient $Na_2CO_3$ is to treat the fibre with a source of insolubilising ions, such as calcium chloride, calcium sulphate or the like, so that some of the sodium ions are replaced by insolubilising ions such as calcium ions. The first order derivative of percentage weight loss of the fibre with temperature retains the two maxima in the range 200° to 300° C. In such treated fibres the higher of the two maxima (that generally found within the range 280°–300° C.) tends to be reduced to a shoulder on the lower of the two maxima (that generally found with a maximum in the range of 200°–250° C.) However, the skilled worker will appreciate that a shoulder represents a second peak and the two peaks may be separately drawn using standard computer aided calculations if desired.

Alginate fibres employed in the absorption of proteinaceous material according to the present invention may have medicaments incorporated therein. Suitable medicaments include those which aid recovery of wounds, for example an antifungal agent (such as metronidazole), an antibacterial agent (such as chlorhexidine), nisin a polypeptide obtainable in nature by various strains of the bacterium *Streptococcus lactis,* an angionenisis promoting agent or the like. Fibres incorporating medicaments are prepared by the treatment thereof with an aqueous solution of the medicament or its salt.

It is one of the surprising advantages of the high absorbency fibres employed in this invention that they can be swollen, dried (for example with acetone) and rehydrated and still retain their high absorbency. This allows for ready sterilization, for example by drying, irradiating and rehydrating.

It has further been found that hyaluronic acid can be incorporated into fibres according to the present invention.

Hyaluronic acid (hereinafter referred to as HA) is a natural high viscosity mucopolysaccharide, generally having a molecular weight range of $3\times10^3$ to $8\times10^6$ Daltons (although there are reports of HA having molecular weights as high as $13\times10^6$) depending on source, method of isolation and method of determination. The isolation and characterisation of HA are described in Meyer, et a., J. Biol. Chem. 107, 629, (1934); J. Biol. Chem. 114, 689, (1936); Balazs, Fed. Proc. 17, 1086, (1958); Laurent, et al., Biochem. Biophys. Acta. 42, 476, (1960); Weissman, et al., J. Am. Chem. Soc., 76, 1753, (1954); and Meyer, Fed. Proc. 17, 1075, (1958).

HA is normally employed as its sodium salt although some other salting ions such as potassium or calcium or the like may also be present. All such physiologically acceptable forms and especially the sodium salt are encompassed within the term HA herein.

HA is frequently used in ocular surgery as a replacement for subretinal fluid and vitreous humor. HA can also be used as a replacement for synovial fluid that is lost as a result of surgery or chronic inflammatory disease such as rheumatoid arthritis. HA is also known to be implicated in wound healing and angiogenesis. A wound dressing capable of providing sustained release of hyaluronic acid might therefore be expected to promote wound healing and/or angiogenesis.

There are accordingly further provided use of fibres substantially as hereinbefore described additionally comprising hyaluronic acid, in the absorption of proteinaceous material present in a wound environment into the structure of the fibres.

A suitable average molecular weight range for HA for use in the fibres of the present invention is $1.5\times10^3$ to $2\times10^6$, such as $1\times10^4$ to $1\times10^6$, preferably $1.5\times10^4$ to $1\times10^5$, more preferably about $7.5\times10^4$.

It is believed that the HA incorporated into fibres of the invention resides in spaces or "pockets" in the internal structure of the fibre and that release of the HA from the fibre to the environment of use takes place in a sustained manner as the fibre swells under the conditions of use. For example, fibres according to the present invention containing HA may be formed into a fabric used to prepare a wound dressing. As the dressing absorbs wound exudate, such as proteinaceous material, the fibres swell and HA is delivered to the wound in a sustained manner.

Incorporation of HA into the fibres employed in the invention may be achieved by contacting the fibres with an aqueous solution of HA followed by a suitable aqueous ionic solution, such as a solution of calcium, magnesium or zinc cations, preferably a solution of calcium cations, more preferably aqueous calcium chloride solution.

In some circumstances it is desirable to produce fibres of relatively low absorbency which contains hyaluronic acid for use in the present invention. Use in the absorption of proteinaceous material by such fibres (with absorbency of 5–40 g of water per gram) form an aspect of this invention. Similarly, the use of dressings comprising fibres containing hyaluronic having said absorbency form an aspect of this invention. Such fibres are prepared by the process of hereinbefore described followed by treatment with a source of insolubilising cations, such as calcium ions, for example a solution of calcium chloride, which is sufficiently concentrated and for sufficient time to produce the desired solubility.

Alginate fibres employed according to the present invention are suitably in the form of wound dressings for use in the absorption of proteinaceous material, especially proteases, into the structure of the alginate fibres employed in the dressings.

The alginate fibres of the dressings employed according to the present invention may, for example, be non-woven, woven or knitted and may be prepared by conventional methods. The fibres may be embossed, for example by stitching or calendering regions of the fibres, so as to produce a dressing of increased structural integrity. The dressings may consist essentially of alginate fibres as hereinbefore described or in part of such fibres.

The alginate fibres according to the invention may also be formed into a dressing using wet-laying techniques such as those conventional in the paper industry. Conventional alginate fibres cannot be wet-laid using conventional papermaking techniques. The ability of the fibres employed in the present invention to be wet-laid by conventional methods represents an important advantage of the present fibres over conventional alginate fibres.

The wound dressings may be in the form of a pad or sliver of alginate fibres Most aptly the pad is 0.5 to 7.5 mm thick and is preferably 1 to 5 mm thick, for example 1.5 to 3 mm thick. Typical pad sizes are rectangular with sides of from 4 to 20 cm, for example 5 to 15 cm, 10×10 cm and the like although other shapes may be employed such as circular, oval or the like. Suitably the sliver has a length of from 1 to 40 cm and a diameter of 1 to 3 cm, such as 1.5 to 2.5 cm diameter.

The use of wound dressings according to the present invention suitably includes the treatment of highly exuding wounds such as pressure sores, ulcers, burns and the like, although the dressings could of course be used in the treatment of other wounds such as cuts, sores, blisters, rashes or other lesions or areas of trouble skin.

As used herein, the term "burn" includes burn, scald and the like.

In the management of burns, the affected site is desirably kept continually moistened, since it has been observed that an extremely effective treatment for burns is to allow cool water to penetrate over a prolonged period to the layers of skin underlying the affected area. It is accordingly envisaged that the burn dressing of the present invention would be applied in a wetted state as hereinbefore described for the solubilising of hard eschar prior to the uptake of proteases from the wound environment.

The wound dressings encompassed by the invention may comprise one or more of the wound dressing components well known in the art. For example, the wound dressing may comprise one or more adhesive layers. The wound dressing may also comprise one or more further absorbent layers in addition to the alginate fibres of the invention. Suitably the further absorbent layer or layers is selected from the group consisting of alginate fibres, karaya gum, locust bean gum, guar gum, sodium acrylate, polyvinyl alcohol, pectin, gelatin, carboxymethylcellulose, high molecular weight carbowaxes, carboxy polymethyl collagen and cotton.

Aptly the absorbent layer comprises alginate fibres. Alginates are produced by a variety of micro-organisms and marine algae which are the normal commercial source. The alginates being natural materials show considerable variety but are characterised in being block copolymers, the individual monosaccharide units being arranged into groups as blocks of mannuronic (M) and guluronic (G) residues. In addition to the repeating blocks each polymer chain can contain a proportion of alternating M and G monosaccharide units.

Suitably alginate fibres employed in the absorbent layer may be high M or high G, typically 60–80% by weight M or G respectively. The alginate fibres may be high absorbent fibres substantially as hereinbefore described.

The alginate fibres of the further absorbent layer or layers may, for example, be non-woven, woven or knitted. Preferably, the fabric is non-woven, not only from the standpoint of ease of manufacture but also because of the general dimensional stability of non-woven fabrics, which are acknowledged not to stretch so easily as, for example, knitted fabrics.

In the preparation of a non-woven fabric, a cotton card may be used to form a web, which may then be cross-lapped, for example with a Garnet Bywater cross-lapper, and then needle punched in a Garnet Bywater needle loom. In the preparation of a woven fabric, the precursor alginate fibres may be carded and then spun into a yarn, which can be woven in a conventional loom. Alternatively, the fibres may be collected in a spinning box, according to the method described in British Patent No. 568177, and woven. In the preparation of a knitted fabric, the fibres can be prepared as a continuous filament yarn, again according to the method described in British Patent No. 568177, which is then knitted on a conventional knitting machine.

The wound dressing according to the present invention may further be provided with an occlusive film, which comprises a moisture vapour permeable form, for example a polyurethane, polyetherester derivatives, a polyether amide and the like. Generally the polymers will be hydrophilic, for example as described in EP 0 279 118. Aptly such films will be from 15 to 50 microns thick, more usually 20 to 30 microns, for example 25 microns. The film layer may be applied directly to the surface of the alginate pad but more suitably will be adhered by means of an adhesive, for example as described in WO 90/01954 or EP 0 279 118. Such adhesives are preferably moisture vapour permeable, for example an acrylic, polyurethane or polyether adhesive of which acrylic adhesives are preferred.

The wound dressings employed according to the present invention will advantageously be conventional dressings well known in the art. Examples of suitable dressings include bandages, adhesive strip dressings, island dressings, pads of various kinds, surgical sponges and packs and ward dressings. Such dressings may conveniently be prepared by standard methods known from the art.

The dressings in accordance with the present invention will conveniently be packaged in an hermetically-sealed envelope and sterilised, e.g. with ethylene oxide or by irradiation using gamma rays or an electron beam.

The absorbency of fabric according to the invention may be determined according to the following method.

Test Method 1

The apparatus used in the determination of absorbency is depicted in FIG. 5, and consists of water bath 1 containing a 0.9% (w/w) aqueous saline solution, or deionised water, absorbent strip 2, burette 3, top-pan balance 4 and overflow 5.

The thickness of the absorbent strip 2 is substantially equivalent to that of the dressing 7. The filter paper 8 has substantially the same planar dimensions as the dressing 7, but not necessarily the same thickness.

The apparatus is set up with the surface 6 of the saline solution or water level with the top surface of the top-pan balance 4. The flow of liquid from the burette 3 is then adjusted to approximately 1.5 ml per minute. The absorbent strip 2 is then saturated and placed between the bath 1 and the balance 4, as depicted in FIG. 5. The balance 4 is then tared. A weighed dressing 7 and filter paper 8 (cut to size) is positioned as depicted in FIG. 5. Care must be taken to ensure that the edge of the absorbent strip 2 furthest away from the water bath 1 does not extend beyond the corresponding edge of the dressing 7, as shown in FIG. 5.

After six minutes the weight shown on the balance 4 is recorded. The dressing 7 and filter paper 8 are then removed and any residual weight on the balance 4 noted.

Absorbency is determined on the basis of the following equation:

$$\text{Weight of liquid absorbed} = \text{total weight on balance} - \left[ \text{dry weight of dressing} + \text{weight of saturated filter paper} + \text{residual weight on balance} \right]$$

Test Method 2

The Tanδ value of a fibre was determined by using a Thurlby Thandor TG502 sweep/function generator, a Tectronics 2212 digital storage oscilloscope and a capacitance test cell (plate area 16 square centimeters and fitted with a 22KΩ resistor). The material to be tested was placed in a small engineers vice and the vice closed. The distance between the plates was measured using a vernier calliper and the earth connection made between the vice and the earth terminal of the capacitance test cell. The function generator and oscilloscope were then connected and the amplitude of the applied sinusoidal voltage measured together with the voltage drop across the resistor and the phase angle between the applied voltage signal and current. The frequency of the applied field was then altered and the measurements repeated for many points in the range 5 mHz to 5 MHZ.

The following non-limiting Examples are intended to illustrate the present invention.

EXAMPLE 1

Calcium alginate fibres were spun from a dope solution containing 4 to 6% sodium alginate employing conventional techniques, and 4 g of the resultant calcium alginate fibres were immersed in 1M hydrochloric acid (1 liter) for 20–30 seconds. The degree of acid conversion was determined from the relative intensities of the peaks at 1720 cm$^{-1}$ and 1600 cm$^{-1}$ in the infrared spectrum, to ensure that the degree of conversion was in excess of 95%. The fibre was then washed with water and immersed in saturated saline solution (2 liters). The fibre was then chopped to the required staple length (10 to 30 mm). After cutting to the appropriate length the fibre was dispersed into a stirring vessel containing deionised water (2 liters). The fibres were washed in a stream of running water until they swelled to their maximum extent and no sodium chloride could be detected in the eluent. Sodium carbonate solution (0.1M) was then added in 1 ml aliquots whilst monitoring the pH and conductivity of the medium. Care was taken to ensure that the pH did not exceed 6.5. After the addition of approximately 12 mls of sodium carbonate solution (conductivity meter reading between 180 and 200 micro siemens), the material was filtered and dried with acetone followed by air drying.

The resulting material was a pad of high absorbency alginate fibres suitable for use according to the present invention, whereby proteinaceous material present in a wound environment can be absorbed into the structure of the alginate fibres.

EXAMPLE 2

The product of Example 1 was re-suspended in water (200 cm$^3$) and filtered through a Buchner funnel. Three aliquots (50 cm$^3$) of calcium chloride solution (0.1M) were then slowly filtered through the pad followed by washing with water (200 cm$^3$). The pad was removed and the calcium/sodium content determined by atomic absorption spectrometry (99% calcium, 1% sodium). The pad was then air dried at room temperature.

Similarly this pad can be employed in the absorption of proteinaceous material according to the invention.

EXAMPLE 3

The pad obtained by Example 2 was placed in a knife mill fitted with a 2 mm screen and milled once. The resulting product had an average fibre length of 1 mm, and was suitable for use according to the present invention.

EXAMPLE 4

The sample obtained by Example 2 was placed in a miniature card (WIRA Ltd) and collected, after separation of the fibres, as an amorphous mass.

EXAMPLE 5

This example describes the investigation of protease uptake by fibres employed according to the present invention. The assay employed to determine the total protease activity used azocasein (casein dyed red with a sulphanilamide dye) as a proteolytically—vulnerable protein. After exposure of this substrate to the protease and incubation for a predetermined time, the substrate is separated from the products by acid precipitation and the concentration of product determined spectrophotometrically by virtue of the label.

The product of Example 1 was treated with a calcium chloride solution (1M, 20 cm$^3$) and washed with deionized water (30 cm$^3$) to remove excess calcium and dried. This reprocessed fibre (0.8070 g) was then placed in a recirculating system with 0.008 mg/cm$^3$ protease solution (Sigma, crude from Bovine Pancreas) in TRIS-HCl buffer (pH 7.2). A conventional high G alginate (of the type available under the trade mark KALTOSTAT) (99% Ca, 0.4540 g) was similarly investigated in the recirculating system.

Periodically aliquots (0.2 cm$^3$) were removed and incubated at 37° C. for 10 minutes in azocasein solution (0.11 g/100 cm$^3$ in TRIS HCl buffer pH 7.2). After this time 0.5 cm$^3$ of the incubation was added to 1 ml of 5% (w/v) trichloroacetic acid and centrifuged at 10000×g for 2 minutes to compact the undigested substrate. The supernatant was then removed and its absorbance at 340 nm wavelength determined. Blank determinations were also performed substituting TRIS-HCl buffer (pH 7.2, 0.2 cm$^3$) for recirculating solution.

When the recirculating sample absorbance fell to the level of the blank, further additions of protease solution were made to the recirculating solution. This was continued until further additions of protease resulted in no further decrease in the activity of the protease in the recirculating solution.

Mass of Protease Taken Up

When the rate of uptake slowed down considerably, the reprocessed and high G alginates were removed, patted with filter paper to remove excess solution and weighed. A known mass of each alginate was then dried in an oven at 52° C. to constant mass in order to determine the percentage increase due to protease uptake.

TABLE 1

Protease Recirculation with high G Alginate (99% Ca), available under the trade mark KALTOSTAT.

| Total mass of Protease Recirculated | Time (min) | *Absorbance at 340 nm |
|---|---|---|
| 1.99 mg | 3 | 0.471 |
|  | 20 | 0.264 |
|  | 40 | 0.213 |
|  | 80 | 0.209 |
|  | 195 | 0.220 |
| 7.587 mg | 2 | 0.502 |
|  | 13 | 0.321 |
|  | 25 | 0.314 |
|  | 63 | 0.289 |
| 15.587 mg | 2 | 0.586 |
|  | 16 | 0.444 |
|  | 26 | 0.428 |

*Average blank value = 0.063

TABLE 2

Protease Recirculation with reprocessed fibre employed according to the present invention

| Total mass of Protease Recirculated | Time (min) | *Absorbance at 340 nm |
|---|---|---|
| 1.99 mg | 3 | 0.404 |
|  | 20 | 0.063 |
|  | 40 | 0.060 |
|  | 80 | 0.057 |
|  | 195 | 0.061 |
| 15.587 mg | 2 | 0.242 |
|  | 16 | 0.086 |
|  | 26 | 0.075 |
| 240.587 mg | 2 | 1.000 |
|  | 66 | 0.267 |
|  | 85 | 0.191 |
|  | 100 | 0.238 |
|  | 115 | 0.184 |
| 458.08 mg | 2 | 0.963 |
|  | 40 | 0.284 |
|  | 119 | 0.171 |

*Average Blank value = 0.063

The rate of absorbance decrease with time indicates that the reprocessed fibre employed according to the present invention shows a greater rapidity in protease uptake than the commercially available high G alginate.

The reprocessed fibre employed in the present invention also retained a much greater mass of protease than the commercially available high G alginate. At the end of the experiment a mass of 458.08 mg of protease had been added to the recirculating solution employed in the treatment of the fibre utilised in the present invention, which represented an uptake of 56.8% of protease, based on the weight of the alginate fibre.

From table 1 it can be seen that the high G alginate appears to have reached saturation after only 15.587 mg of protease was added, which represented an uptake of only 4.3% of protease based on the weight of the alginate fibre.

EXAMPLE 6

Two alginate fibre pads prepared according to Example 2 were respectively employed in the treatment of a yellow sloughy wound and a wound covered with a hard eschar.

In both cases, the pads were wetted with saline solution and applied to the wounds. The pads were removed from respective wounds on a once daily basis, by irrigation with a saline solution and excision of the top layer of slough or eschar.

In the case of the sloughy wound the yellow colour was seen to disappear, over a 5 to 6 day period, as the wound became red and granulating due to the uptake of proteases therefrom into the structure of the alginate fibres. The pad was applied to the wound environment for a period of 8 days.

In the case of the wound covered with a hard eschar, the eschar was seen to begin solubilizing after application for 1 to 2 days of the pad to the wound environment. The pad was applied to the wound for a period of 5 days.

EXAMPLE 7

Tanδ values were measured according to Test Method 2 above for a range of fibre samples. The results were as follows:

| Fibre | Peak 1 Hz | Peak 2 Hz | Peak 3 Hz |
|---|---|---|---|
| KALTOSTAT[1] | 6449 | 1000 | 896 |
| KALTOGEL[2] | 578 | 416 | 46 |
| KALTOSTAT acid treated, neutralised and dried. | 2929 | 541 | 54 |
| Fibre prepared as in Example 1. | 0.056 | 0.018 | — |
| As above, treated with calcium ions[3] | 5.412 | 2.928 | 0.464 |

[1]commercially available calcium sodium alginate of high guluronate content
[2]commercially available calcium sodium alginate of high malluronate content
[3]the treatment comprised washing the fibres with three 2M CaCl$_2$ solutions each 200 ml per 1.5 g of fibre followed by washing three times with 200 ml of deionised water.

We claim:

1. Alginate fibres capable of absorbing at least 10% by weight, based on the weight of the alginate fibres, of proteinaceous material into the structure of the fibres.

2. Alginate fibres as claimed in claim 1 wherein the fibres absorb at least 30%, based on the weight of the alginate fibres, of proteinaceous material into the structure of the alginate fibres.

3. Alginate fibres as claimed in claim 1 wherein the proteinaceous material is protease.

4. Alginate fibres as claimed in claim 1 wherein the fibres are characterised by having two maxima in a plot of the first order derivative of percentage weight loss of the fibre with temperature against temperature in the range of 100° to 400° C.

5. Alginate fibres as claimed in claim 4 wherein the fibres are characterised by having two maxima in the plot of the first order derivative of percentage weight loss with temperature against temperature in the range 200° to 300° C.

6. Alginate fibres as claimed in claim 1 wherein the fibres are obtainable by a process comprising the following steps:
   (1) treating alginate fibres with a suitable acid so as to produce fibres comprising approximately 90–98% alginic acid fibres;
   (2) treating the alginic acid fibres with a saturated aqueous solution of mono- or divalent cations;
   (3) washing the fibres with water until imbibition of water by the fibres has effectively ceased; and
   (4) treating the fibres with a source of a cation capable of forming a water-soluble alginate salt.

7. Alginate fibres as claimed in claim 6 wherein the alginate fibres in step (1) are calcium alginate.

8. Alginate fibres as claimed in claim 6 wherein other ions and/or medicaments are included after or during step 4.

9. Alginate fibres as claimed in claim 6 wherein the fibres comprise hyaluronic acid or a pharmaceutically acceptable salt thereof.

10. Alginate fibres as claimed in claim 1 wherein the fibres are characterised by having a glass transition range of less than 30° C.

11. Alginate fibres as claimed in claim 1 wherein the fibres are characterised by having a Tanδ value in the range from 0 to 15 Hz.

12. Alginate fibres as claimed in claim 1 wherein the fibres comprise a mixed salt alginate which has first and second cations, the first cation being capable of forming an insoluble alginate salt and the second cation being capable of forming a soluble alginate salt where the ratio of first to second cations is 70:30 to 100:0 by weight.

13. Alginate fibres as claimed in claim 12 wherein the first cation is calcium and the second cation is sodium.

14. Alginate fibres as claimed in claim 12 wherein the ratio of first to second cations is 80:20 to 100:0 by weight.

15. Alginate fibres as claimed in claim 1 wherein the fibres have an absorbency of at least 40.0 grams of deionized water per gram of fibres.

16. Alginate fibres as claimed in claim 1 wherein the fibres have an absorbency of at least 60 times their own weight of deionized water.

17. A method of treating a wound comprising the steps of applying alginate fibres to a wound environment so as to effect uptake of slough into the structure of the fibres.

18. A method of treating a wound as claimed in claim 17 wherein the fibres are applied in a wet state.

19. A method as claimed in claim 17 wherein the alginate fibres are applied to the wound for a period selected from one to sixteen days.

20. An alginate fabric for use in the absorption of proteinaceous material from a wound environment, the fabric formed in whole or in part from alginate fibres capable of absorbing at least 10% by weight, based on the weight of the alginate fibres, of the proteinaceous material into the structure of the fibres.

21. A wound dressing comprising an alginate fabric as claimed in claim 20 in the form of a sterile dressing for the treatment of a burn or ulcer or other exuding wound.

* * * * *